(12) United States Patent
Brannan et al.

(10) Patent No.: US 8,968,290 B2
(45) Date of Patent: Mar. 3, 2015

(54) MICROWAVE ABLATION GENERATOR CONTROL SYSTEM

(75) Inventors: Joseph D. Brannan, Erie, CO (US);
Kyle R. Rick, Boulder, CO (US);
Manoja Weiss, Arvada, CO (US);
Joshua C. Glazier, Littleton, CO (US)

(73) Assignee: Covidien LP, Mansfield, MA (US)

( * ) Notice: Subject to any disclaimer, the term of this patent is extended or adjusted under 35 U.S.C. 154(b) by 441 days.

(21) Appl. No.: 13/419,981

(22) Filed: Mar. 14, 2012

(65) Prior Publication Data

US 2013/0241769 A1 Sep. 19, 2013

(51) Int. Cl.
*A61B 18/18* (2006.01)

(52) U.S. Cl.
USPC ............................................ 606/33; 607/101

(58) Field of Classification Search
USPC ...................... 606/33, 41; 607/101
See application file for complete search history.

(56) References Cited

U.S. PATENT DOCUMENTS

| | | | |
|---|---|---|---|
| 5,300,068 A | 4/1994 | Rosar et al. | |
| 5,961,871 A | 10/1999 | Bible et al. | |
| 6,471,696 B1 | 10/2002 | Berube et al. | |
| 6,784,405 B2 | 8/2004 | Flugstad et al. | |
| D574,323 S | 8/2008 | Waaler | |
| 2002/0087151 A1 | 7/2002 | Mody et al. | |
| 2006/0155270 A1* | 7/2006 | Hancock et al. | 606/33 |
| 2006/0184163 A1* | 8/2006 | Breen et al. | 606/20 |
| 2008/0015570 A1 | 1/2008 | Ormsby et al. | |
| 2008/0058793 A1* | 3/2008 | Pilla et al. | 606/33 |
| 2009/0018536 A1 | 1/2009 | Behnke | |
| 2009/0093801 A1* | 4/2009 | Crossman | 606/21 |
| 2010/0063494 A1* | 3/2010 | Orszulak | 606/33 |
| 2010/0079215 A1 | 4/2010 | Brannan et al. | |
| 2010/0082022 A1 | 4/2010 | Haley et al. | |
| 2010/0082023 A1 | 4/2010 | Brannan et al. | |
| 2010/0082024 A1 | 4/2010 | Brannan et al. | |
| 2010/0082025 A1 | 4/2010 | Brannan et al. | |
| 2010/0082083 A1 | 4/2010 | Brannan et al. | |
| 2010/0082084 A1 | 4/2010 | Brannan et al. | |
| 2010/0125269 A1 | 5/2010 | Emmons et al. | |
| 2010/0298822 A1 | 11/2010 | Behnke | |
| 2011/0213355 A1 | 9/2011 | Behnke, II | |

FOREIGN PATENT DOCUMENTS

| | | |
|---|---|---|
| DE | 179607 | 3/1905 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |

(Continued)

OTHER PUBLICATIONS

U.S. Appl. No. 10/406,690, filed Apr. 3, 2003, Robert J. Behnke, II.

(Continued)

*Primary Examiner* — Allen Porter, Jr.

(57) ABSTRACT

A microwave energy delivery and measurement system, including a microwave generator and a microwave energy delivery device, for performing medical procedures, and a remote power coupler system for measuring one or more parameters of the microwave energy signal including a remote RF sensor housed in the microwave energy delivery device and a power coupler processer coupled with the processing unit of the microwave energy delivery device.

8 Claims, 5 Drawing Sheets

(56) References Cited

FOREIGN PATENT DOCUMENTS

| | | |
|---|---|---|
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008058737 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 882635 | 12/1998 |
| EP | 1051948 | 11/2000 |
| EP | 1366724 | 1/2006 |
| EP | 880220 | 6/2006 |
| EP | 1776929 | 4/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 2434872 | 8/2007 |
| JP | 63 005876 | 1/1988 |
| SU | 166452 | 1/1965 |
| SU | 727201 | 4/1980 |
| WO | WO 94/26188 | 11/1994 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO 2006/069013 | 6/2006 |
| WO | WO2008/053532 | 5/2008 |
| WO | WO2008/071914 | 6/2008 |

OTHER PUBLICATIONS

U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/362,548, filed Jan. 31, 2012, Steven P. Buysse.
U.S. Appl. No. 13/362,816, filed Jan. 31, 2012, Steven P. Buysse.
U.S. Appl. No. 13/424,127, filed Mar. 19, 2012, Robert J. Behnke, II.
U.S. Appl. No. 13/426,204, filed Mar. 21, 2012, Robert B. Smith.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.

(56) References Cited

OTHER PUBLICATIONS

Zlatanovic M., "Sensors in Diffusion Plasma Processing" Microelectronics 1995; Proceedings 1995; 20$^{th}$ International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860. dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
International Search Report dated Jun. 26, 2013 in copending International Application No. PCT/US2013/028327.

* cited by examiner

MICROWAVE ABLATION GENERATOR CONTROL SYSTEM

BACKGROUND

1. Technical Field

The present invention relates to systems, devices and methods for performing a medical procedure, wherein the system, apparatus and method includes the measurement of at least one parameter related to the microwave energy delivered to the handpiece of the microwave energy delivery device.

2. Description of Related Art

During microwave ablation procedures, the electrical performance of the microwave energy delivery system (e.g., the system including a generator, a microwave energy delivery device, a waveguide configured to delivery the microwave energy signal from the generator to the handpiece of the device, and an antenna) changes throughout the course of an ablation treatment. The change in performance may be due to a change in the delivery device, a change in the tissue properties or a change in the delivery path. The ability to observe parameters indicative of these changes provides better control of the delivery of the microwave energy.

For example, measuring antenna impedance is a common method for determining antenna performance and/or a change in an antenna property. Microwave systems are typically designed to a characteristic impedance, such as, for example, 50 Ohms, wherein the impedance of the generator, the delivery system, the ablation device and tissue are about equal to the characteristic impedance. Efficiency of energy delivery decreases when the impedance of any portion of the system changes.

With low frequency RF systems impedance can easily be determined by measuring the delivered current at a known voltage and calculating tissue impedance using well known algorithms. Obtaining accurate measurements of tissue impedance at microwave frequencies is more difficult because circuits behave differently at microwave frequency. For example, unlike an electrode in an RF system, an antenna in a microwave system does not conduct current to tissue. In addition, other components in a microwave system may transmit or radiate energy, like an antenna, or components may reflect energy back into the generator. As such, it is difficult to determine what percentage of the energy generated by the microwave generator is actually delivered to tissue, and conventional algorithms for tissue impedance are typically inaccurate.

Therefore, other methods of measuring impedance are typically used in a microwave system. One well known method is an indirect method using measurements of forward and reverse power. While this is a generally accepted method, this method can also prove to be inaccurate because the method fails to account for component losses and depends on indirect measurements, such as, for example forward and reverse power measurements from directional couplers, to calculate impedance. In addition, this method does not provide information related to phase, a component vital to determining antenna impedance.

The present disclosure describes a microwave energy delivery system that includes a microwave energy delivery device configured to measure at least one parameter related to the energy delivered to the handpiece of the microwave energy delivery device.

SUMMARY

The present disclosure relates to a microwave energy delivery and measurement system, including a microwave generator and a microwave energy delivery device, for performing medical procedures. In one aspect of the invention, the microwave energy delivery and measurement system includes a microwave generator for delivery of a microwave energy signal and a microwave energy delivery device configured to receive the microwave energy signal. The microwave generator includes a processing unit configured to control the generation and delivery of the microwave energy signal at a predetermined microwave frequency and configured to receive one or more measurement signals, related to the microwave energy signal, from the microwave energy delivery device. The microwave generator also includes a directional coupler configured to generate and provide one or more generator measurement signals related to forward power and/or reverse power of the microwave energy signal at the microwave generator to the processing unit. The microwave energy deliver device includes a housing, a microwave antenna coupled to the housing and configured to receive the microwave energy signal and resonate at the predetermined microwave frequency, a remote RF sensor and a remote sensing interface. The remote RF sensor is disposed in the housing, coupled to the microwave antenna and configured to generate and provide one or more remote measurement signals. The remote sensing interface is coupled between the processing unit of the microwave generator and the remote RF sensor. The remote sensing interface is configured to receive one or more remote measurement signals from the remote RF sensor and to provide remote measurement signals to the processing unit.

In other aspects of the present disclosure, the remote RF sensor may include a remote directional coupler. Further, a remote measurement signal from the remote sensing interface may be related to forward power and/or reverse power of the microwave energy signal at the remote directional coupler.

In other aspects of the present disclosure, the remote sensing interface may include one or more conductors coupled between the microwave energy delivery device and the microwave generator or the remote sensing interface may generate a wireless connection between the microwave energy delivery device and the microwave generator.

In other aspects of the present disclosure, the processing unit may be configured to adjust a parameter related to the microwave energy signal based on a property of a generator measurement signal and/or a remote measurement signal. The processing unit may include a comparator configured to generate a comparator signal related to a comparison of a generator measurement signal and a remote measurement signal. The generator measurement signals and/or the remote measurement signals may be related to forward power and/or related to reverse power.

In other aspects of the present disclosure, the remote RF sensor may include a remote directional coupler and an intermediate frequency generator connected to the remote directional coupler. The remote directional coupler may be configured to generate an unconditioned measurement signal at a predetermined frequency related to the microwave energy signal. The intermediate frequency generator connected to the remote directional coupler is configured to mix each of the unconditioned measurement signals with a carrier signal thereby generating an intermediate measurement signal related to each measurement signal generated by the remote directional coupler.

In other aspects of the present disclosure, the intermediate frequency generator may include an oscillator and a power mixer. The oscillator may be configured to generate the carrier signal at a carrier signal frequency. The power mixer may be configured to generate an intermediate measurement signal by mixing the carrier signal and a unconditioned measurement signal generated by the remote directional coupler. The remote measurement signal provided by the remote RF sensor interface to the microwave generator may include an intermediate measurement signal generated by the power mixer.

In other aspects of the present disclosure, the processing unit may include an electrosurgical generator processing unit and a remote power coupler processing unit. The electrosurgical generator processing unit may be configured to control the generation and delivery of the microwave energy signal at the predetermined microwave frequency. The remote power coupler processing unit may be configured to receive a remote measurement signal related to the microwave energy signal and configured to provide the remote measurement signal to the electrosurgical generator processing unit. In one aspect of the present disclosure, the remote power coupler processing unit is an add-on device incorporated into an electrosurgical generator.

Aspects of the present disclosure may include a light-weight directional coupler for measuring a property of a microwave energy signal. The light-weight directional coupler may include a through-signal coaxial cable and a coupled coaxial cable, each including an inner conductor and an outer conductor formed in a coaxial relationship, abutting and parallel to each other along a length thereof. The through-signal coaxial cable and the coupled coaxial cable each define a first slot having a first length and a second slot having a second length therein. The first and second slots are adjacent each other to operatively couple the through-signal coaxial cable and the coupled coaxial cables to each other.

In other aspects of the present disclosure, each slot may be formed by removing a portion of the outer conductor thereby forming a half-cylinder opening at each slot. The slot length of each of the first slot and the second slot may be equal and the spacing between the first slot and the second slot along the length may be equal. The spacing between the first slot and the second slot may be equal to one-quarter of a wavelength ($\lambda/4$) of the microwave energy signal provided to the through-signal coaxial cable. The first slot length and the second slot length may be between 13 mm and 15 mm.

BRIEF DESCRIPTION OF THE DRAWINGS

Various aspects of the present disclosure are described hereinbelow with reference to the drawings, wherein.

DETAILED DESCRIPTION

Figure 1:
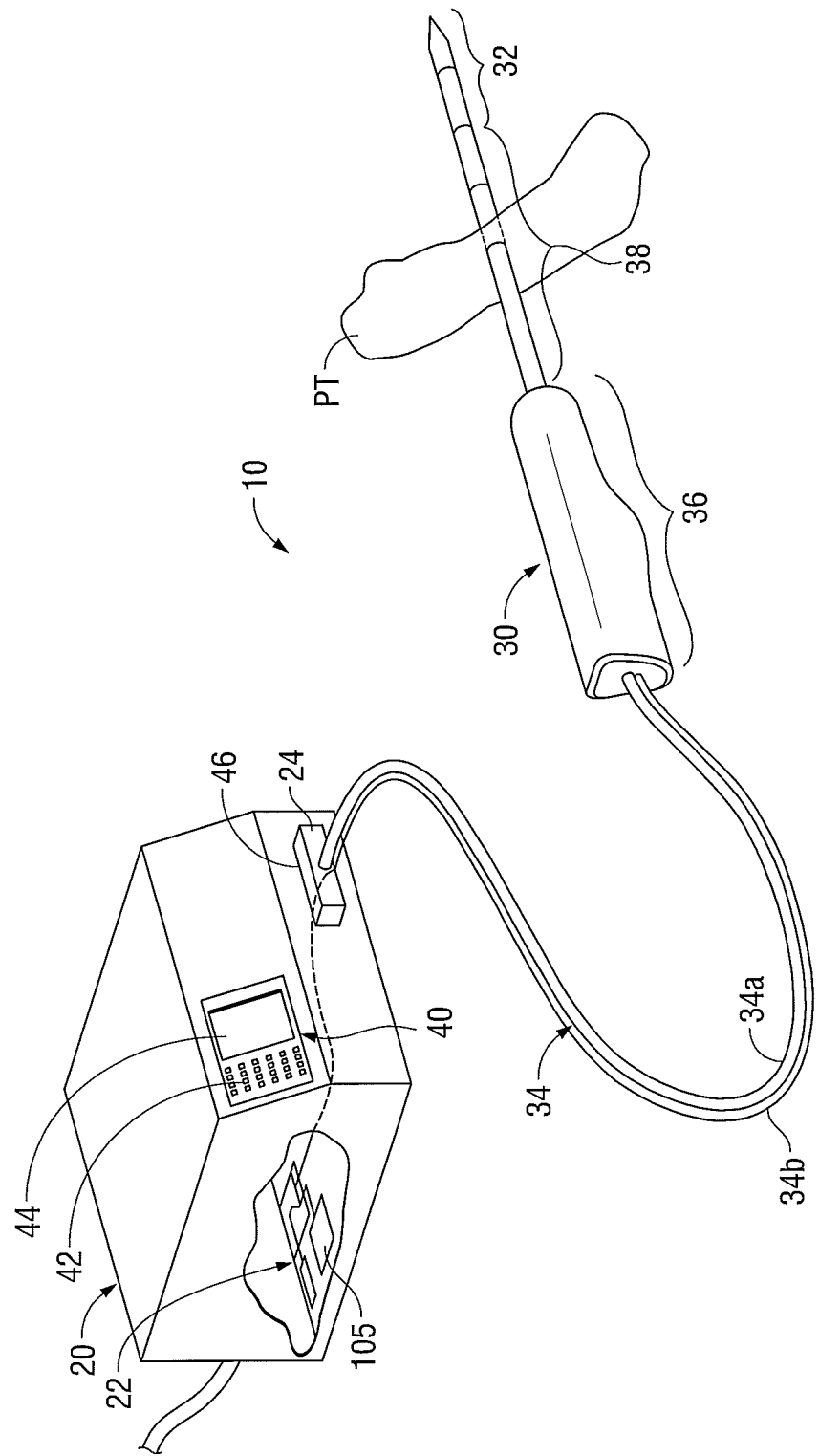
FIG. 1 is a perspective view of microwave energy delivery system according to an embodiment of the present disclosure.

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to employ the present disclosure in virtually any appropriately detailed structure.

In the drawings and in the descriptions that follow, the term "proximal," as is traditional, will refer to an end which is closer to the user, while the term "distal" will refer to an end that is farther from the user.

Referring now to FIG. 1, a system for supplying microwave energy for microwave therapy, according to an embodiment of the present disclosure, is shown as 10. The microwave energy delivery system 10 includes an electrosurgical generator 20 with a control circuit 22 for controlling the operation of the electrosurgical generator 20 and a microwave energy delivery device 30 coupled to the electrosurgical generator 20 via a transmission line 34.

Transmission line 34 includes a coaxial cable 34a (i.e., a waveguide) and an auxiliary cable 34b. The coaxial cable 34a is configured to deliver a microwave energy signal between the electrosurgical generator 20 and the handpiece 36 of the microwave energy delivery device 30. The auxiliary cable 34b is configured to deliver one or more signals between the handpiece 36 and the electrosurgical generator 20. The one or more signals delivered between the handpiece 36 and the electrosurgical generator 20 may include a DC power signal for powering circuitry in the handpiece 36 and an information signal containing real-time or historical information related to a condition and/or a quality of the microwave energy signal at the handpiece 36, the shaft 38 (extending from the handpiece 36) and/or the antenna 32 (on the distal end of the microwave energy delivery device 30) that radiates therapeutic energy therefrom.

A transmission line connector 24 disposed on the proximal end of the transmission line 34 connects to a transmission line receiver 46 on the electrosurgical generator 20. A distal end of the transmission line 34 connects to the microwave energy delivery device 30.

Electrosurgical generator 20 may include an operator interface 40 having a keypad 42 for entering parameters related to electrosurgical generator 20, the microwave energy delivery device 10 and/or parameters related to the delivery of microwave energy. Display 44 may indicate or graph one or more parameters related to the delivery of microwave energy and/or one or more parameters related to the microwave generator 20, transmission line 34 and/or microwave energy delivery device 10.

Microwave energy delivery device 30 includes handpiece 36, shaft 38 and antenna 32 formed on the distal end of the shaft 38. One suitable microwave energy delivery device 30, as illustrated in FIG. 1, is a tissue penetrating microwave energy delivery device 30 sold by Covidien under the trademark Evident™ Microwave Ablation Surgical Antennas although the embodiments described herein may be suitable for any device capable of delivering microwave energy or the like. The embodiments described herein may also be applied to any suitable energy delivery device as explained in more detail below.

Figure 2:
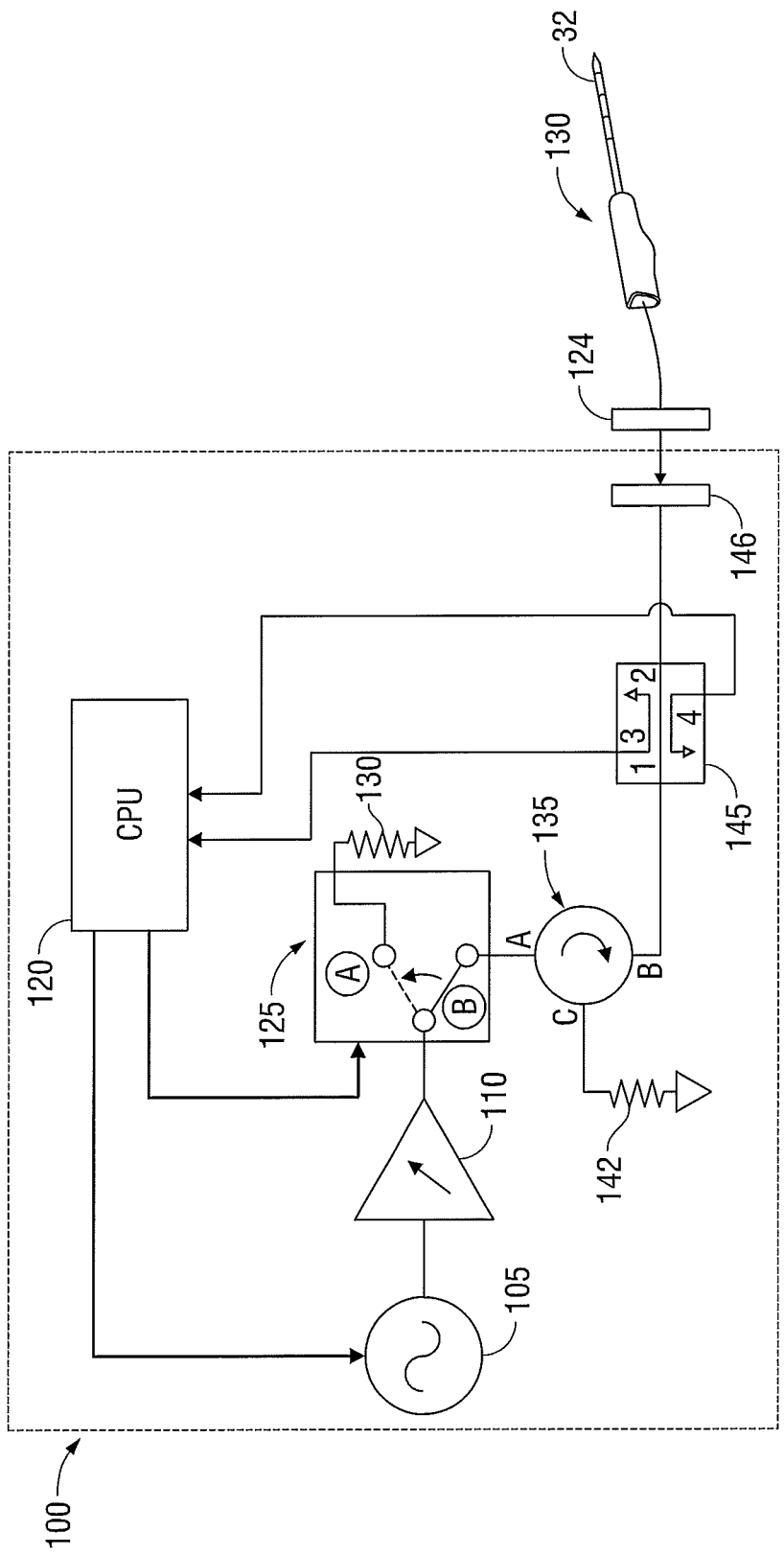
FIG. 2 is a control circuit, electrical block diagram of a typical electrosurgical generator.

Referring to FIG. 2, the control circuit, electrical block diagram of a typical electrosurgical generator 20 is shown generally designated control circuit 100. For clarity, the control circuit 100 of the electrosurgical generator 20 only provides the general functionality of a control circuit of a typical microwave generator 20 and does not include all aspects of a microwave generator 20. The functionality of individual components may be combined or included in one or more components and the various components are interconnected with suitable cables and/or connectors.

The control circuit 100 includes a signal generator 105 capable of generating and supplying a high frequency microwave signal to an amplifier 110. Signal generator 105 may be a single frequency generator, may include variable frequency capability or may include the capability of providing a signal that includes two or more related frequencies wherein the microwave energy delivery device 30 (See FIG. 1) is configured to resonate at the two or more related or unrelated frequencies.

Amplifier 110 receives and amplifies the high frequency microwave signal from the signal generator 105 to a desirable energy level. Amplifier 110 may include a single-stage or multi-stage amplifier and may include one or more signal conditioning circuits or filters (not shown) such as, for example, a low-pass filter circuit, a high-pass filter circuit or a bandpass filter circuit. Amplifier 110 gain may be fixed or controlled by a suitable controller, such as, for example, a control algorithm in the supervisory control system (not shown), a central processing unit 120 (CPU) or the gain of the amplifier 110 may be manually adjusted by a clinician through the keypad 42 (See FIG. 1).

Amplifier 110 supplies a continuous, amplified microwave signal to a hot switch relay 125. Hot switch relay 125 is controlled by the CPU 120 and configured to switch the amplified microwave signal to one of an amplifier burn-off load resistor 130 and a circulator 135. For example, in position A the hot switch relay 125 delivers energy to burn-off load resistor 130 and in position B delivers energy to the circulator 135.

Hot switch relay 125 may be any suitable solid-state high power switch capable of switching a high power microwave energy signal. Hot switch relay 125 receives the high power microwave signal from the signal generator 105 and amplifier 110, and passes the signal between the amplifier burn-off load resistor 130 and the circulator 135 without powering down the signal generator 105 or amplifier 110. In use, the hot switch relay 125 allows the electrosurgical generator 20 to provide near instantaneous power (e.g., can provide nearly continuous power with very rapid on/off capabilities) without creating amplifier transients, by eliminating the need to power down the signal generator 105 or amplifier 110.

Amplifier burn-off load resistor 130 may be any suitable coaxial terminator capable of dissipating microwave energy while generating a minimal amount of voltage standing wave ratio (VSWR), or reflective energy, over the bandwidth of the signal generator 105.

Circulator 135 is a passive three port device that eliminates standing waves between the hot switch relay 125 and the directional coupler 145. Circulator 135 passes signals received on Port A to Port B, signals received on Port B to Port C and signals received on Port C to Port A. When hot switch relay 125 is in Position A, the microwave energy signal is passed from Port A of the circulator 135 to the directional coupler 145 connected to Port B. Reflected energy from the directional coupler 145 (e.g., the transmission line receiver 146 connected to the transmission line 134 and the microwave energy delivery device 130) received on Port B, is passed to Port C and dissipated through the reverse energy burn-off load resistor 142. Reverse energy burn-off load resistor 142 is similar in function to the amplifier burn-off load resistor 130 as discussed hereinabove.

Directional coupler 145 may be configured to operate like most conventional directional couplers known in the available art. Directional coupler 145 passes the high power microwave energy signal received on Port 1 to Port 2 with minimal insertion loss. Energy is reflected back through the transmission line receiver 46 (from the transmission line 134 and microwave energy delivery device 30) and received on Port 2 of the directional coupler 145, passed through the directional coupler 145 and out Port 1 of the directional coupler 145, and to Port B of the circulator 135. Circulator 135 passes the energy received through Port B to Port C of the circulator 135 and the energy is dissipated by the reverse energy burn-off load resistor 142.

Directional coupler 145 samples a small portion of each of the signals received on Port 1 and Port 2 and passes the small portion of each signal to Ports 3 and 4, respectively. The signals on Port 3 and 4 are proportional to the forward and reverse power, respectively, and provided to the CPU 120.

The forward and reverse power signals from the directional coupler 145 are measured by a measurement system (e.g., contained in the CPU 120) configured to obtain samples of the signals. The measurements are taken continuously or periodically, thereby providing an indirect measurement of the delivered energy (i.e., forward power) and the reflected energy (reverse power). These power measurements from a directional coupler 145 positioned in the microwave generator 20 are limited to characteristics of the microwave energy signal supplied to the transmission line receiver 146 and are not necessarily the same characteristics of the microwave energy signal received by the microwave energy delivery device 30 and not necessarily the same characteristics of the microwave energy signal delivered to patient tissue by the antenna 32.

Figure 3:
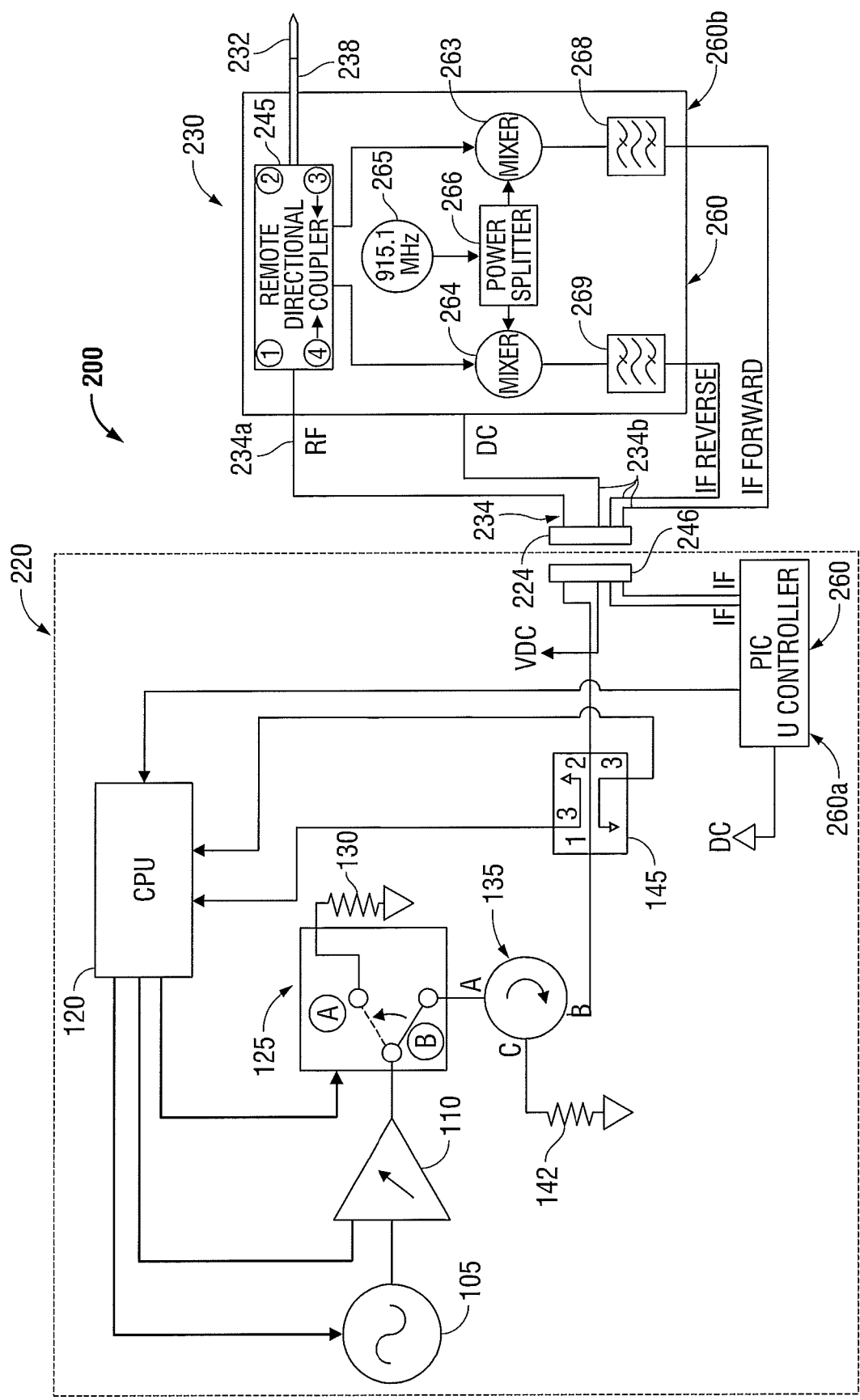
FIG. 3 is a control circuit, electrical block diagram of a microwave energy delivery system according to an embodiment of the present disclosure.

FIG. 3 is a control circuit block diagram of a microwave energy delivery system according to an embodiment of the present disclosure and is generally designated as 200. For clarity, the control circuit block diagram 200 of the electrosurgical generator 20 only provides general functionality and does not include all aspects of a microwave generator 20. The functionality of individual components may be combined or included in one or more components and the various components are interconnected with suitable cables and/or connectors.

The control circuit block diagram 200 includes components in the electrosurgical generator 220 and components in the microwave energy delivery device 230 connected through the transmission line 234. Transmission line connector 224 on the proximal end of the transmission line 234 connects to the transmission line receiver 246 on the electrosurgical generator 220 and the distal end of the transmission line 234 connects to the microwave energy delivery device 230. Transmission line 234 includes a coaxial cable 234a for transmitting the microwave energy signal between the microwave generator 220 and the microwave energy delivery device 230 and an auxiliary cable 234b. The auxiliary cable 234b may include a remote RF power cable (DC Power), a forward measurement signal cable, a reverse measurement signal cables and an information signal cable for transmitting real-time or historical information related to a condition and/or the quality of the microwave signal in the microwave energy delivery device 230.

The microwave generator 220 includes a processing unit (CPU 120) configured to control the generation and delivery of a microwave energy signal at a predetermined microwave frequency. The CPU 120 is further configured to receive measurement signals related to the microwave energy signal at various locations in the microwave energy delivery system. For example, the CPU 120 receives a measurement signal related to the microwave energy signal within the microwave generator 220 from the dual directional coupler 145 housed in the microwave generator 220 and also receives a measurement signal related the microwave energy signal within the microwave energy delivery device 230 from a remote RF sensor 260b. The CPU 120, by receiving information related to the microwave energy at various locations in the delivery path, is able to determine energy losses at various locations in the system and may perform adjustments to the microwave energy signal based on the information received. The measurement signals generated by the directional coupler 145 and the remote RF sensor 260b may be related to forward power, reverse power, forward and reverse power as discussed in detail hereinbelow.

Figure 4A:
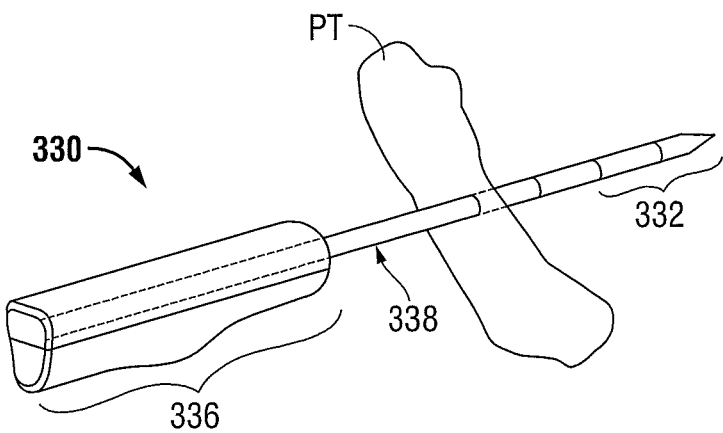
FIG. 4A is a perspective view of the microwave energy delivery device including a compact remote directional coupler.

The functional blocks of the remote power coupler system 260 includes the power coupler processor 260a and the remote RF sensor 260b. The remote RF sensor 260b is housed in the microwave energy delivery device 230 and includes a remote directional coupler 245, a remote oscillator 265, a remote power splitter 266, remote forward power mixer 263 and remote reverse power mixer 264, remote forward intermediate signal transmitter 268 and remote reverse intermediate signal transmitter 269. The individual components of the remote RF sensor 260b and their functionality may be performed by a single device or component. Remote RF sensor 260b is positioned between the transmission line 234 and the antenna 232 and may be housed in the handpiece 336 (as illustrated in FIG. 4a) or housed in the shaft 238.

The remote power coupler processor 260a is housed in and/or directly connected to the electrosurgical generator 220 and coupled to the remote RF sensor 260b. The remote RF sensor 260b generates one or more signals related to the microwave energy signal that passes through the remote RF sensor 260b. The signals generated by the remote RF sensor 260b are directly or indirectly provided to the remote power coupler processor 260a (e.g., wirelessly transmitted or transmitted via one or more conductors in the remote sensing interface cable 234b). The remote power coupler processor 260a processes the signals and/or data from the remote RF sensor 260b and provides the characteristics, signals and/or values related to the measured microwave energy signal (e.g., the signal provided to the remote RF sensor 260b) to the CPU 120 in the electrosurgical generator 220.

In one embodiment, the remote power coupler processor 260a is an internal or external plug-in card and/or add-on device that may be incorporated into the electrosurgical generator 220. For example, remote power coupler processor 260a may be removably connected to a port such as, for example, a serial data port, a communication port or a direct bus connection port. In another embodiment, the functionality of the remote power coupler processor 260a is incorporated into the CPU 120 of the electrosurgical generator 220.

The remote directional coupler 245 proportionally divides the forward power microwave energy signal, generated by the electrosurgical generator 220 and provided to Port 1, between an unconditioned forward power measurement signal on Port 3 and a forward microwave energy signal on Port 2. The forward power measurement signal on Port 3 is provided to a forward power mixer 263 and the forward energy signal on Port 2 is provided to the antenna 232. The unconditioned forward power measurement signal is converted, conditioned and provided to the remote power coupler processor 260a as discussed hereinbelow.

At least a portion of the forward microwave energy signal from Port 2 is reflected back from the transmission path between Port 2 and/or the antenna 232. The reflected energy (e.g., the reverse signal) is provided to Port 2 and a portion of the reverse signal is proportionally divided between an unconditioned reverse power measurement signal on Port 4 and a reverse microwave energy signal on Port 1. The unconditioned reverse power measurement signal on Port 4 is provided to a forward power mixer 264 and converted, conditioned and provided to the remote power coupler processor 260a as discussed hereinbelow.

The forward and reverse power mixers 263 and 264 receive a carrier signal, generated by the oscillator 265 and split by the power splitter 266. The forward and reverse power mixers 263 and 264 also receive the respective unconditioned forward and reverse power measurement signal from the remote directional coupler 245. The forward and reverse power mixers 263, 264 each mix the carrier signal with the respective unconditioned forward and reverse power measurement signals thereby down-converting the unconditioned forward and reverse measurements signals to forward and reverse intermediate frequency IF signals in the kHz range. For example, as illustrated in FIG. 3, the remote RF sensor 260b may be configured to down-convert the unconditioned forward and reverse measurement signals from 915 MHz to an IF signal frequency of 100 kHz using a carrier signal of 915 MHz.

The forward and reverse IF signals from the mixers 263 and 264 are provided to the forward and reverse power transmitters 268 and 269, respectively, and are transmitted to the remote power coupler processor 260a. Signals may be transmitted via one or more conductors in the remote sensing interface cable 234b or signals may be digitized by the forward and reverse power transmitters and wirelessly transmitted to the remote power coupler processor 260a. Power transmitters 268, 269 may condition the forward and reverse IF signals by filtering and/or amplifying the forward and reverse IF signals prior to transmission. Power transmitters 268, 269 may be configured to transmit information related to the forward and reverse IF signals to the remote power coupler processor 260a (e.g., gains values and information related to the carrier signal). The information from the power transmitters 268, 269 may be conveyed through a separate information signal cable included as part of the auxiliary cable 234b, added to the forward and reverse IF signals or wirelessly transmitted to the remote power coupler processor 260a.

The remote power coupler processor 260a converts the forward and reverse IF signals to a digital signal, extracts information from the digital signals and/or the conveyed information and provides the extracted information to the CPU 120 of the electrosurgical generator 20. The extracted information may include signal amplitude, phase information, phase relationships information (e.g., phase relationship between the forward and the reflected signals) and/or reflection coefficients.

In one embodiment, a pre-measurement calibration procedure calibrates the remote directional coupler 245 prior to delivering energy to patient tissue. The pre-measurement calibration procedure may include performing measurements under various loaded and/or unloaded conditions (e.g., short, open and matched load conditions). Measurements from one or both directional couplers 145, 245 during the pre-measurement calibration procedure may be used in the electrosurgical energy delivery algorithm and/or the control algorithm. Alternatively, in another embodiment the calibration of the remote directional coupler 245 may allow the directional coupler 145 in the electrosurgical generator 220 to be temporarily bypassed and/or eliminated.

In yet another embodiment, a calibration procedure that calibrates (or re-calibrates) the remote directional coupler 245 is performed during the energy delivery procedure or as a step in the electrosurgical energy delivery control algorithm and/or the control algorithm.

Electrosurgical generator 220 may modify, pause or terminate energy delivery if one or more measurements or values from the remote power coupler system 260 exceed a threshold, the difference between one or more values exceeds a threshold or a changing in a value exceeds a threshold. In another embodiment, the electrosurgical generator 220 determines the viability (e.g., useful life and/or expected life) of one or more components of the electrosurgical system, such as, for example, the viability of the cable 334, the viability of microwave energy delivery device 330 and/or the viability of one or more components thereof.

In another embodiment, the CPU 120 utilizes a measurement, data or a signal from the remote power coupler system 260 (power coupler processor 260a and/or remote RF sensor 260b) to determine a change in the condition of the energy delivery pathway and/or change in the condition of the target tissue. For example, the CPU 120 may determine that a change occurred in one or more parameters or the CPU 120 may determine that a change in the rate of change occurred in one or more parameters. The change may indicate a condition, may indicate a change in the tissue, may indicate a change in a tissue property and/or may be used to predetermine or predict a condition. The CPU 120 may use the calculated change or calculated rate of change to modify an operation parameter, to modify an energy delivery parameter and/or to determine the viability of one or more components of the electrosurgical system.

In another embodiment the use of the change of a parameter, the rate of change of a parameter, and/or the comparison of a change and/or a rate of change of a parameter at the directional coupler 145 and/or the remote RF sensor 260b may eliminate the need to calibrate the remote directional coupler 245 since the actual value is irrelevant and used only to determine if a change has occurred. For example, when energy delivery is initiated, the CPU 120 may record an initial snapshot of the microwave energy signal (e.g., the various parameters related to the microwave energy signal) at the directional coupler 145 and at the remote RF sensor 260b. The initial snapshot may be used as an energy delivery baseline to determine any changes in delivered energy or any changes in the energy delivery pathway.

In another embodiment, the CPU 120 compares the change of the forward power measured at the directional coupler 145 to the change of the forward power at the remote RF sensor 260b to determine if the power loss, or rate of power loss, at the electrosurgical generator 220 varies from the measurements at the remote RF sensor 260b. The CPU 120 may also compare the calculated change of the reverse power, measured at the direction coupler 145, to the calculated change of the reverse power, measured at the remote RF sensor 260b. The comparison may determine if the change in the reflected power at the directional coupler 145 varies from the change in the reflected power at the remote RF sensor 260b.

In another embodiment, the CPU 120 compares the calculated rate of change of the reverse power measurement at the remote directional coupler 245 to the calculated rate of change of the forward power measurement at the remote RF sensor 260b to measure a rapidly changing event, such as a change in tissue property. Change in tissue property will be observed through a change in reflected power at both directional couplers 145 and 245. The comparison may also be used to predict a condition and to control energy delivery based on the prediction. By using the change or rate of change, the relative accuracy of the measurements is not relevant to measurements of change or measurements of the rate of change.

In another embodiment, the CPU 120 compares the forward power measurement at the remote directional coupler 245 with the forward power measurement at the directional coupler 145 to determine the forward power losses in the cable 234a or to determine a change in the forward power losses in the cable 234a. Additionally, or alternatively, the CPU may compare the reverse power measurement at the remote directional coupler 245 with the reverse power measurement at the directional coupler 145 to determine a change in the reverse power losses in the cable 234a or to determine a change in the reverse power losses in the cable 234a.

Another embodiment of the present disclosure is a light-weight coaxial coupler suitable for placement and use in the handpiece 336 of a microwave energy delivery device 230. A commonly used coaxial coupler, manufactured and sold from MECA Electronics of Denville, N.J., is rated for a maximum power of 500 W, has a directivity of 25 dB and a coupling of 30 dB and weighs approximately 1 pound. As such, this commonly used coaxial coupler, while providing the desired functionality for the remote directional coupler, may not be commercially successful because of the additional and excessive weight the commonly used coaxial coupler would add to the microwave energy delivery device 230.

Figure 4B:
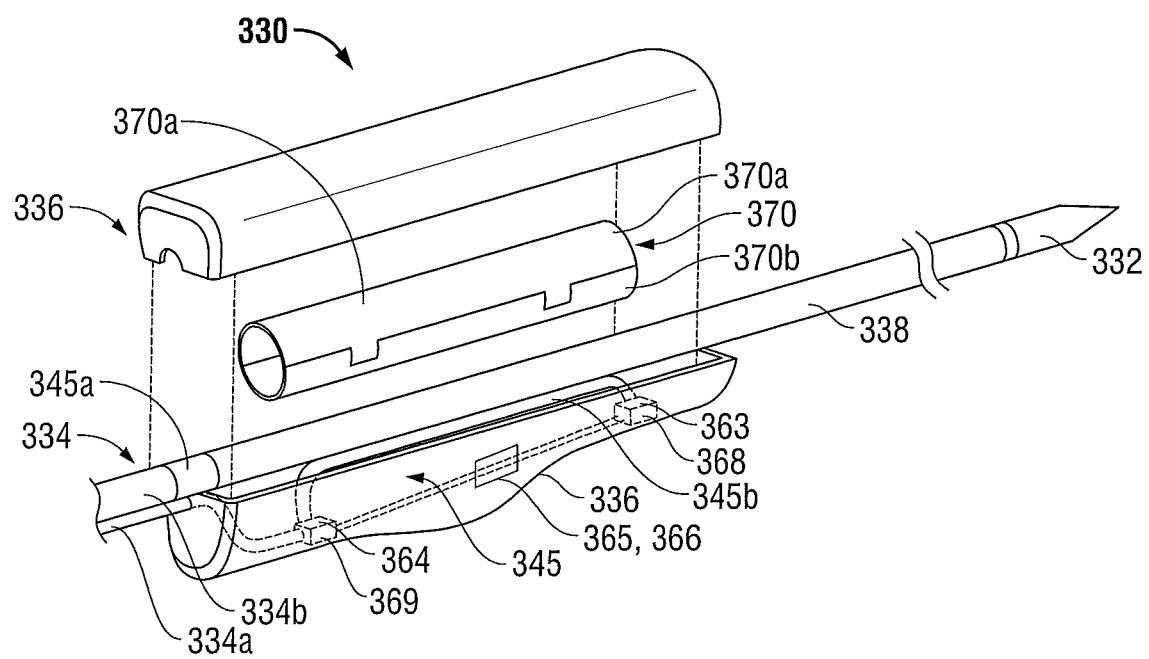
FIG. 4B is an exploded view of the microwave energy delivery device including a compact remote directional coupler of FIG. 4A.

FIG. 4A is a perspective view and FIG. 4B is an exploded view of a microwave energy delivery device 330 including a light-weight remote directional coupler 345 according to another embodiment of the present disclosure. The light-weight remote directional coupler 345, which is part of the remote power coupler system 260 discussed hereinabove, is integrated into the handpiece 336. The space requirements of the light-weight remote directional coupler 345 may require slight or no enlargement of the handpiece 336 and adds approximately 100 grams to the overall weight of the microwave energy delivery device 330 thereby making the addition of a remote power coupler system 260, described hereinabove, a feasible addition to any microwave energy delivery system.

As illustrated in FIG. 4B, the light-weight remote directional coupler 345 includes a through-signal coaxial cable 345a and a coupled coaxial cable 345b. The through-signal coaxial cable 345a is part of, or connects to, the shaft 338 and receives a microwave energy signal from the coaxial cable 334a of the transmission line 334. The coupled coaxial cable 345b connects to the remote forward and reverse mixers 363, 364. The remote forward and reverse power mixers 363, 364 connect to the remote power splitter 366 and receive a carrier signal generated by the remote oscillator 365 therefrom. In use, the light-weight remote directional coupler 345 provides a forward power measurement signal and a reverse power measurement signal to the respective mixer 363 and 364. The mixers 363 and 364 down-converts the respective measurement signal using the carrier signal and the down-converted signals are provided to the auxiliary cable 334a by the forward and reverse power transmitters 368, 369 as discussed hereinabove.

Figure 5:
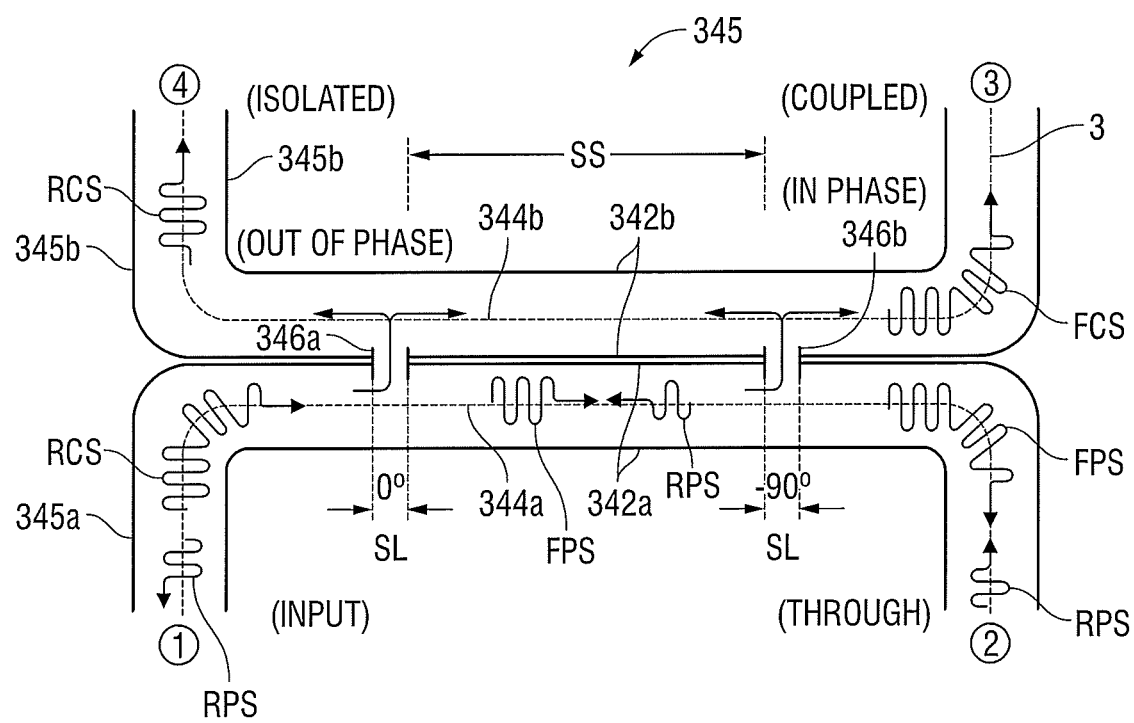
FIG. 5 is a functional block diagram of a remote directional coupler according to an embodiment of the present disclosure.

FIG. 5 is a functional block diagram of the light-weight remote directional coupler 345 according to an embodiment of the present disclosure. The light-weight remote directional coupler 345 measures one or more properties of a microwave energy signal and includes the through-signal coaxial cable 345a and the coupled coaxial cable 345b. Each of the through-signal coaxial cable 345a and the coupled coaxial cable 345b includes an inner conductor 344a, 344b and an outer conductor 342a, 342b, respectively, formed in a coaxial relationship therebetween. The outer conductors 342a, 342b of the through-signal coaxial cable 345a and the coupled coaxial cable 345b each include a first slot 346a and a second slot 346b formed therein. The first and second slots 346a, 346b are formed to allow coupling between the two cables 345a, 345b.

The labels provided on each cable 345a, 345b correspond to standard marking for a directional coupler with the input signal indicated as Port 1, the through signal indicated as Port 2, the forward coupled signal indicated as Port 3 and the reverse coupled signal indicated as Port 4. As such, the through-signal coaxial cable 345a connects to the coaxial cable 334a of the transmission line 334 on Port 1 and the antenna 332 on Port 2 and the coupled coaxial cable 345b connects to the remote forward mixer 363 on Port 3 (providing a forward coupled signal thereto) and the remote reverse mixer 364 on Port 4 (providing a reverse coupled signal thereto).

In one embodiment, the slots 346a, 346b are created by stripping away part of the outer conductor 342a, 342b on each cable 345a, 345b. For each slot 346a, 346b, half of the outer conductor 342a, 342b was removed thereby forming a half-cylinder opening at each slot 346a, 346b. As illustrated in FIG. 5, the length of each slot 346a, 346b is indicated by a slot length "SL" and the spacing between the slots 346a, 346b is indicated by the slot spacing "SS".

The performance and/or operational parameters of the light-weight remote directional coupler 345 are a function of slot spacing "SS" and slot length "SL". The slot spacing SS is the distance between the inner edge of each slot 346a, 346b and the slot length "SL" is the opening width of each slot 346a, 346b. The slot spacing "SS" is related to the length of one-quarter of the microwave signal wavelength. Simulations performed with varying slot spacing "SS" and varying slot lengths "SL" determined that modification of the slot spacing "SS" resulted in large variations in the directivity. For example, in one simulation, modification of the slot spacing "SS" by as little as 0.5 mm resulted in changes in the directivity. To prevent any bending or repositioning of the position of the cable 345a, 345b the sections containing the first and second slots 346a, 346b are fixed with respect to each other and with respect to the handpiece 336.

As illustrated in FIG. 5, the slots 346a, 346b are positioned about one-quarter of a wavelength ($\lambda/4$) apart (e.g., 5.5 cm at 915 MHz using standard RG 58 cable) to allow the forward power signal to add in phase in Port 3 and to add out of phase in Port 4. Similarly, the reverse power signal will add in phase at Port 4 and add out of phase at Port 3. As such, only the forward coupled signal remains on Port 3 and the reverse coupled signal remains on Port 4.

Simulations conducted with varying slot lengths SL resulted in directivity between 25 dB and 42 dB with slot lengths between about 13 mm and 15 mm. Obviously, variations in the slot spacing "SS" and the slot length "SL" may provide other variations and are within the scope of the present disclosure.

Returning to FIG. 4B, exposing the inner conductors 344a and 344b, as discussed hereinabove, may result in an undesirable release of radiation from the handpiece 336. As such, a metallic shield 370 configured to encircle at least the first and second slots 346a, 346b may be added to reduce and/or eliminate any undesirable radiation released from the handpiece 336. In one embodiment, the metallic shield 370 is formed from a first shield member 370a and a second shield member 370b that connect together and form a tube-like the metallic shield 370.

Simulations conducted with a metallic shield 370 resulted in a reduction of the directivity to approximately 25 dB and a decrease in the coupling factor between the through-signal coaxial cable 345a and the coupled coaxial cable 345b.

In another embodiment, at least a portion of the remote RF sensor 260b illustrated in FIGS. 3, 4B and 4B and discussed hereinabove are formed with microstrip or stripline construction. The construction may include a conducting strip and a ground plane separated by a dielectric substrate. The microstrip may include any portion of the remote RF sensor 260b, 361 described herein including any one or more of the remote directional coupler 245, the oscillator 265, the power splitter 266, the mixers 263, 264 and the power transmitters 268, 269.

One example of a directional coupler made in microstrip or stripline construction is a branch-line coupler. A branch-line coupler may be formed by two main transmission lines shunt-connected by two secondary, or branch, lines. The two main transmission lines and the two secondary lines form a geometry such that the four ports have a 90 degree phase difference between the two input ports and two output ports of the two main transmission lines.

In one embodiment, the circuitry housed in the handpiece 336 is formed of a microstrip circuit wherein the transmission cable 334 connects to a first coaxial connector formed on the proximal end of the microstrip circuit and the shaft 338 connects to a second coaxial connector formed on the distal end of the microstrip circuit.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A microwave energy delivery and measurement system, comprising:
   a microwave generator configured to generate a microwave energy signal, the microwave generator including:
      a processing unit configured to control the generation and delivery of a microwave energy signal; and
      a directional coupler configured to provide at least a portion of the microwave energy signal to the processing unit; and
   a microwave energy delivery device configured to couple to the microwave generator, the microwave energy delivery device including:
      a housing;
      a microwave antenna coupled to the housing and configured to receive the microwave energy signal;
      a remote RF sensor disposed in the housing and coupled to the microwave antenna, the remote RF sensor including a remote directional coupler, a first mixer, and a second mixer, the remote directional coupler configured to provide a forward power measurement signal to the first mixer and a reverse power measurement signal to the second mixer; and
   a remote sensing interface configured to couple the processing unit of the microwave generator to the remote RF sensor and to transmit at least one of the forward power measurement signal or the reverse power measurement signal from the remote RF sensor to the processing unit.

2. The system according to claim 1, wherein the remote sensing interface includes one or more conductors coupled between the microwave energy delivery device and the microwave generator.

3. The system according to claim 1, wherein the remote sensing interface generates a wireless connection between the microwave energy delivery device and the microwave generator.

4. The system according to claim 1, wherein the processing unit is configured to adjust a parameter related to the microwave energy signal based on at least one of the microwave energy signal, the forward power measurement signal, or the reverse power measurement signal.

5. The system according to claim 1, wherein the processing unit further includes a comparator configured to compare at least one of a portion of the microwave energy signal, the forward power measurement signal, or the reverse power measurement signal.

6. The system according to claim 1, wherein the remote RF sensor further includes
- an oscillator configured to generate a carrier signal at a carrier signal frequency and
- wherein the first mixer is configured to generate an intermediate forward signal by mixing the carrier signal and the forward power measurement signal and the second mixer is configured to generate an intermediate reverse signal by mixing the carrier signal and the reverse power measurement signal.

7. The system according to claim 1, wherein the processing unit includes an electrosurgical generator processing unit and a remote power coupler processing unit, wherein the electrosurgical generator processing unit is configured to control the generation and delivery of the microwave energy signal and the remote power coupler processing unit is configured to receive at least one of a portion of the microwave energy signal, the forward power measurement signal, or the reverse power measurement signal and to provide at least one of a portion of the microwave energy signal, the forward power measurement signal, or the reverse power measurement signal to the electrosurgical generator processing unit.

8. The system according to claim 7, wherein the remote power coupler processing unit is an add-on device incorporated into the microwave generator.

* * * * *